United States Patent
Goto et al.

(10) Patent No.: US 11,097,269 B2
(45) Date of Patent: Aug. 24, 2021

(54) MICROFLUIDIC DEVICE AND SAMPLE ANALYSIS METHOD

(71) Applicant: TOPPAN PRINTING CO., LTD., Tokyo (JP)

(72) Inventors: Keisuke Goto, Tokyo (JP); Yoichi Makino, Tokyo (JP); Akihiro Hoshino, JP (JP)

(73) Assignee: TOPPAN PRINTING CO., LTD., Tokyo (JP)

( * ) Notice: Subject to any disclaimer, the term of this patent is extended or adjusted under 35 U.S.C. 154(b) by 44 days.

(21) Appl. No.: 15/945,272

(22) Filed: Apr. 4, 2018

(65) Prior Publication Data

US 2018/0221877 A1  Aug. 9, 2018

Related U.S. Application Data

(63) Continuation of application No. PCT/JP2016/079956, filed on Oct. 7, 2016.

(30) Foreign Application Priority Data

Oct. 8, 2015 (JP) .............................. JP2015-200361

(51) Int. Cl.
*B01L 3/00* (2006.01)
*G01N 21/03* (2006.01)
(Continued)

(52) U.S. Cl.
CPC ........ *B01L 3/502715* (2013.01); *B81B 1/006* (2013.01); *B81B 3/0083* (2013.01);
(Continued)

(58) Field of Classification Search
CPC ....... B01L 2300/0829; B01L 3/502715; B01L 2300/0877; B01L 2300/168;
(Continued)

(56) References Cited

U.S. PATENT DOCUMENTS

2003/0219713 A1* 11/2003 Valencia ............ G01N 15/1475
435/4
2005/0221281 A1* 10/2005 Ho ...................... G01N 21/6452
435/4
(Continued)

FOREIGN PATENT DOCUMENTS

JP     11-211653    8/1999
JP      3326708     9/2002
(Continued)

OTHER PUBLICATIONS

International Search Report dated Nov. 8, 2016 in corresponding International Patent Application No. PCT/JP2016/079956.

*Primary Examiner* — Lyle Alexander
*Assistant Examiner* — Bryan Kilpatrick (57) ABSTRACT

A microfluidic device includes: a base plate allowing an electromagnetic wave to pass therethrough and having no autofluorescence; a microwell array formed on the base plate and including a wall layer in which a plurality of through-holes are formed in a thickness direction; and a lid member disposed opposite to the base plate in a state of being separated from the wall layer, wherein microwells are formed by the base plate and the through-holes formed in the wall layer, and wherein the wall layer is formed of a material containing a colored component that absorbs an electromagnetic wave of a predetermined wavelength.

12 Claims, 8 Drawing Sheets

(51) Int. Cl.
*G01N 33/52* (2006.01)
*B81B 3/00* (2006.01)
*B81B 1/00* (2006.01)
*G01N 21/64* (2006.01)
*B01L 7/00* (2006.01)

(52) U.S. Cl.
CPC ......... *G01N 21/03* (2013.01); *G01N 21/6428* (2013.01); *G01N 21/6452* (2013.01); *G01N 33/52* (2013.01); *B01L 7/52* (2013.01); *B01L 2300/046* (2013.01); *B01L 2300/0829* (2013.01); *B01L 2300/0877* (2013.01); *B01L 2300/0887* (2013.01); *B01L 2300/161* (2013.01); *B81B 2201/057* (2013.01); *B81B 2201/058* (2013.01); *B81B 2203/0338* (2013.01); *B81B 2203/0353* (2013.01); *G01N 2021/6439* (2013.01)

(58) Field of Classification Search
CPC ......... G01N 21/6428; G01N 2021/058; G01N 2021/6439; G01N 21/6452; G01N 33/52; B81B 1/006; B81B 2203/0338; B81B 2203/0353; B81B 3/0083; B81B 1/00; B81C 1/00
See application file for complete search history.

(56) References Cited

U.S. PATENT DOCUMENTS

| | | | |
|---|---|---|---|
| 2012/0015828 A1* | 1/2012 | Ozawa | B01L 3/50273 |
| | | | 506/7 |
| 2013/0004967 A1 | 1/2013 | Halverson et al. | |
| 2013/0099143 A1 | 4/2013 | Mogami et al. | |

FOREIGN PATENT DOCUMENTS

| | | |
|---|---|---|
| JP | 3510882 | 3/2004 |
| JP | 2007-292556 | 11/2007 |
| JP | 2012-13551 | 1/2012 |
| WO | WO 2015/115635 A1 | 8/2015 |

\* cited by examiner

|  | 350/420nm | 480/530nm | 590/610nm |
|---|---|---|---|
| EXAMPLE 1 | 232 | 270 | 120 |
| COMPARATIVE EXAMPLE 1 | 1651 | 2081 | 10065 |

|  | 350/420nm | 480/530nm | 590/610nm |
|---|---|---|---|
| PRESENCE OF PIGMENT | 172 | 195 | 119 |
| ABSENCE OF PIGMENT | 1371 | 1960 | 585 |

MICROFLUIDIC DEVICE AND SAMPLE ANALYSIS METHOD

CROSS REFERENCE TO RELATED APPLICATIONS

This application is a continuation application based on a PCT Patent Application No. PCT/JP2016/079956, filed Oct. 7, 2016, whose priority is claimed on Japanese Patent Application No. 2015-200361, filed on Oct. 8, 2015, the entire contents of which are hereby incorporated by reference.

BACKGROUND OF THE INVENTION

Field of the Invention

The present invention relates to a microfluidic device having a microwell array, and a sample analysis method using the microfluidic device.

Priority is claimed on Japanese Patent Application No. 2015-200361, filed on Oct. 8, 2015, the content of which is incorporated herein by reference.

Description of the Related Art

In recent years, microwell arrays having various types of fine flow path structures formed using an etching technique or a photolithography technique which is used in a semiconductor circuit manufacturing technique, or a fine plastic molding method have been examined. Wells of these microwell arrays are used as chemical reaction vessels for carrying out various biochemical or chemical reactions in a minute volume of fluid.

Hard substances such as silicone and glass, soft substances such as various polymer resins such as polydimethylsiloxane (PDMS), and silicone rubber, or the like are used as materials for manufacturing a microfluidic device having a microwell array. For example, Japanese Patent Nos. 3510882 and 3326708, and Japanese Unexamined Patent Application. First Publication No. H11-211653 disclose that such a microfluidic device is used as various microchips and biochips.

In recent years, a technique for inspecting a biological substance by performing an enzyme reaction in a minute space having a small volume has been attracting attention. An example of new approaches in nucleic acid detection and quantification include a digital PCR technique. The digital PCR technique is a technique in which a mixture of a reagent and a nucleic acid is divided into innumerable microdroplets and subjected to PCR amplification so that a signal such as fluorescence is detected from droplets containing the nucleic acid, and quantification is performed by counting the droplets from which a signal has been detected.

A method for preparing microdroplets by dividing a liquid with a sealing liquid, a method for preparing microdroplets by placing a reagent in a hole formed on a base plate, and then, placing a sealing liquid on the reagent, or the like is studied as a method for preparing microdroplets.

A method for reducing autofluorescence by adding a pigment to a material constituting a fluid device used in a fluid system for acquiring a fluorescence value emitted from a biomolecule in the fluid system has been studied (refer to, for example, Japanese Patent Nos. 3510882 and 3326708, and Japanese Unexamined Patent Application, First Publication No. H11-211653). This is because detection of autofluorescence derived from the material as noise causes a problem in detecting a fluorescent signal.

SUMMARY

There are several difficulties in applying the technique disclosed in Japanese Patent No. 3510882 to a microfluidic device.

First, the size of a microwell will be described. Since microwells are extremely small, in a case where pigments are added thereto to form a microwell array, the particle diameters of the pigments may be close to the sizes of the microwells. Therefore, there is a possibility that the microwells cannot be formed with high accuracy.

Next, a generation source of autofluorescence which becomes noise will be described. Since the volume of droplets contained in the microwells is extremely small, a fluorescence value emitted is also extremely small. Accordingly, even a minute amount of autofluorescence which has not been considered as a problem in the related art becomes noise having a fluorescence value comparable to the fluorescence of the droplets, which may affect measurement. As will be described in detail below, the generation source of such autofluorescence is not limited to the material forming the microwell array. For this reason, it is difficult to completely solve the problem by merely reducing the autofluorescence of the material.

Based on the above-described circumstances, an object of the present invention is to provide a microfluidic device in which microwells are accurately formed while suppressing autofluorescence of a material.

Another object of the present invention is to provide a sample analysis method capable of analyzing a sample contained in a microwell by suitably excluding minute fluorescent noise.

A microfluidic device according to a first aspect of the present invention includes: a base plate allowing an electromagnetic wave to pass therethrough and having no autofluorescence; a microwell array formed on the base plate and including a wall layer in which a plurality of through-holes are formed in a thickness direction; and a lid member disposed opposite to the base plate in a state of being separated from the wall layer, wherein microwells are formed by the base plate and the through-holes formed in the wall layer, and wherein the wall layer is formed of a material containing a colored component that absorbs an electromagnetic wave of a predetermined wavelength.

In the first aspect, the colored component may be a pigment, and a particle diameter of the pigment may be less than or equal to one fifth of a minimum dimension of each of the microwells.

A sample analysis method according to a second aspect of the present invention is a sample analysis method in which the microfluidic device according to the above-described first aspect is used, and the method includes: supplying a sample into each of the microwells (sample supply step); sealing the sample in each of the microwells using a sealing liquid (sealing step); irradiating the microfluidic device with an electromagnetic wave after sealing the sample in each of the microwells (electromagnetic wave irradiation step); and observing, from the base plate side, the microwell irradiated with the electromagnetic wave (sample observation step).

According to the above-described microfluidic device in the first aspect of the present invention, it is possible to provide a microfluidic device in which microwells are accurately formed while suppressing autofluorescence of a material.

In addition, according to the above-described sample analysis method in the second aspect of the present invention, it is possible to analyze a sample contained in a microwell by suitably excluding minute fluorescent noise.

DETAILED DESCRIPTION OF THE PREFERRED EMBODIMENTS

An embodiment of the present invention will be described with reference to FIGS. 1 to 6. In the present specification, the dimensional ratios in each drawing are exaggerated for explanation, and do not necessarily coincide with the actual dimensional ratio.

Figure 1:
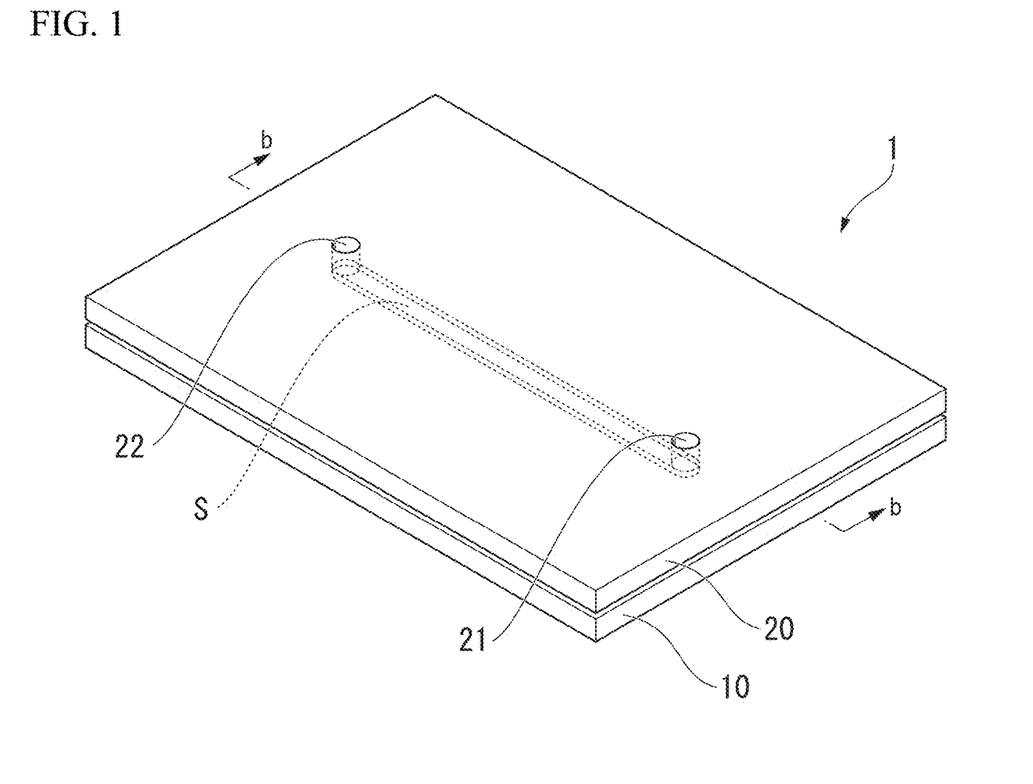
FIG. 1 is a perspective view showing a microfluidic device according to an embodiment of the present invention.
Figure 2:
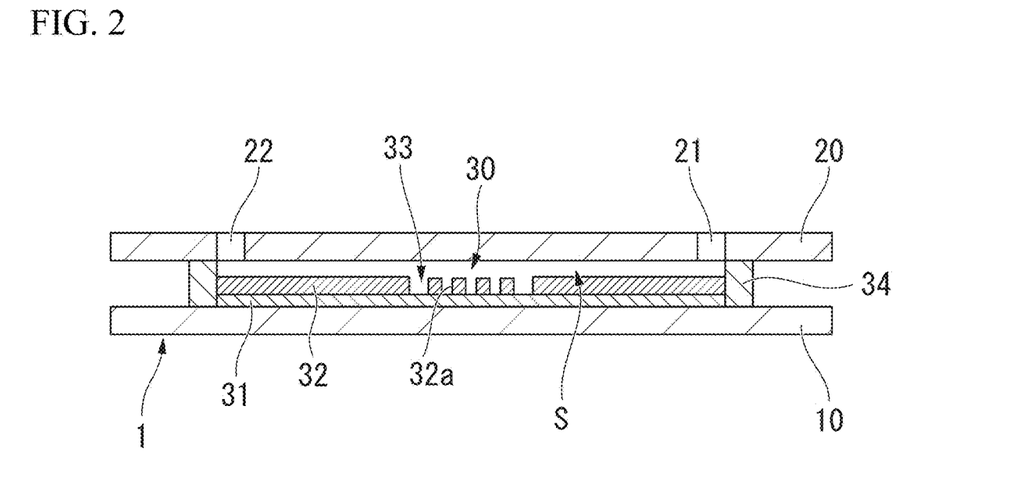
FIG. 2 is a cross-sectional view taken along line b-b of FIG. 1.

FIG. 1 is a perspective view showing a microfluidic device 1 according to the present embodiment. FIG. 2 is a cross-sectional view taken along line b-b of FIG. 1. As shown in FIGS. 1 and 2, the microfluidic device 1 includes a base plate 10, a lid member 20, and a microwell array 30. The lid member 20 is disposed opposite to the base plate 10. The microwell array 30 is provided between the base plate 10 and the lid member 20.

The base plate 10 allows electromagnetic waves to pass therethrough. Here, examples of the electromagnetic waves include X-rays, ultraviolet rays, visible rays, and infrared rays. Since the base plate 10 allows electromagnetic waves to pass therethrough, it is possible to observe fluorescence, phosphorescence, and the like occurring in a sample sealed in the microfluidic device 1 from the side of the base plate 10.

The base plate 10 may allow only electromagnetic waves within a predetermined wavelength range to pass therethrough. For example, in a case where fluorescence having a peak in a wavelength range of 350 to 700 nm which is a visible light region is detected with respect to a sample in a microwell, a base plate which allows visible light at least in the above wavelength range to pass therethrough may be used.

Examples of the material for forming the base plate 10 include glass, resin, and the like. Examples of the resin base plate include an ABS resin, a polycarbonate resin, a cycloolefin copolymer (COC), a cycloolefin polymer (COP), an acrylic resin, polyvinyl chloride, a polystyrene resin, a polyethylene resin, a polypropylene resin, polyvinyl acetate, polyethylene terephthalate (PET), and polyethylene naphthalate (PEN). These resins may contain various additives, or a plurality of resins may be mixed.

Since fluorescence or phosphorescence is used in the sample analysis method to be described below, a material having substantially no autofluorescence is used as the base plate 10. Here, "having substantially no autofluorescence" means that the base plate has no autofluorescence of the wavelength used for detecting experimental results or the effect is weak enough not to affect the detection of the experimental results even if it has autofluorescence. For example, it can be said that the effect is weak enough to affect the detection of the experimental results if the autofluorescence is less than or equal to about one half or less than or equal to about one tenth compared with the fluorescence to be detected.

The thickness of the base plate 10 can be appropriately determined, but is preferably, for example, less than or equal to 5 millimeters (mm), more preferably less than or equal to 2 mm, and still more preferably less than or equal to 1.6 mm.

The lid member 20 is a member formed in a plate shape or a sheet shape and has a first hole 21 and a second hole 22 penetrating in the thickness direction. The first hole 21 and the second hole 22 communicate with an internal space S including the microwell array 30 in the finished microfluidic device 1. The first hole 21 and the second hole 22 each function as an inlet for supplying a fluid to the internal space and an outlet for discharging a fluid.

The material forming the lid member 20 and the thickness of the lid member 20 can be the same as those of the base plate 10.

The electromagnetic wave transparency of the lid member 20 can be appropriately set. That is, in a case where the electromagnetic wave irradiation step to be described below is not performed from the lid member 20 side, the lid member 20 may not allow electromagnetic waves to pass therethrough.

The microwell array 30 has a bottom layer 31, a wall layer 32, and a plurality of microwells 33. The bottom layer 31 is provided on the base plate 10. The wall layer 32 is formed on the bottom layer 31. The plurality of microwells 33 are formed of the bottom layer 31 and a plurality of through-holes 32a formed in the thickness direction of the wall layer 32. The plurality of microwells 33 are formed in an array shape in the wall layer 32. In the internal space S between the base plate 10 and the lid member 20, there is a gap between the microwell array 30 (wall layer 32) and the lid member 20. This gap functions as a flow path that communicates with the plurality of microwells 33 and the first hole 21 and the second hole 22.

The bottom layer 31 forms the bottom surfaces of the microwells 33. Accordingly, in a case where it is desired to impart hydrophilicity to the bottom surfaces, the bottom layer 31 may be formed of a hydrophilic material. In addition, in a case where it is desired to impart hydrophobicity to the bottom surfaces, the bottom layer 31 may be formed of a hydrophobic material. The bottom layer 31 is preferably formed so that the bottom layer 31 allows electromagnetic waves to pass therethrough so as not to obstruct observation of a sample in the microwells 33 from the base plate 10 side. In addition, it is preferable to use a material having substantially no autofluorescence in the bottom layer 31. Here, a base plate in which the base plate 10 and the bottom layer 31 are integrated can be simply referred to as a base plate.

If it is no problem that the characteristics of the base plate 10 are the same as the characteristics of the bottom surfaces of the microwells 33, the wall layer 32 may be formed directly on the base plate 10 without providing the bottom layer 31. Accordingly, in these cases, the surface of the base plate 10 and the through-holes 32a of the wall layer 32 form the microwell 33.

The wall layer 32 is formed of a colored material and has a plurality of through-holes 32a provided in an array shape when seen in the thickness direction. The inner surface of each through-hole 32a forms the inner wall surface of each microwell 33.

Examples of the material for forming the wall layer 32 include a material obtained by mixing a colored component which absorbs an electromagnetic wave of a predetermined wavelength with a resin.

Both a hydrophilic resin in which molecules of constituent components of the resin have a hydrophilic group and a hydrophobic resin in which molecules of constituent components of the resin have a hydrophobic group can be used as the resin material in consideration of the characteristics required for the microwells 33.

Examples of the hydrophilic group include a hydroxyl group, a carboxyl group, a sulfone group, a sulfonyl group, an amino group, an amide group, an ether group, and an ester group. As examples of the hydrophilic resin, a hydrophilic resin from a siloxane polymer; an epoxy resin; a polyethylene resin; a polyester resin; a polyurethane resin; a polyacrylamide resin; a polyvinyl pyrrolidone resin; acrylic resins such as a polyacrylic acid copolymer; polyvinyl alcohol resins such as cationized polyvinyl alcohol, silanolated polyvinyl alcohol, and sulfonated polyvinyl alcohol; a polyvinyl acetal resin; a polyvinyl butyral resin; a polyethylene polyamide resin; a polyamide polyamine resin; cellulose derivatives such as hydroxymethyl cellulose and methyl cellulose; polyalkylene oxide derivatives such as polyethylene oxide and a polyethylene oxide-polypropylene oxide copolymer; maleic anhydride copolymers; ethylene-vinyl acetate copolymers; styrene-butadiene copolymers; and a combination of the above-described resins can be appropriately selected and used.

As examples of the hydrophobic resin, a material having a contact angle of greater than or equal to 70 degrees measured in accordance with a sessile drop method regulated in JIS R3257-1999 can be appropriately selected and used from a novolac resin; an acrylic resin; a methacrylic resin; a styrene resin; a vinyl chloride resin; a vinylidene chloride resin; a polyolefin resin; a polyamide resin; a polyimide resin; a polyacetal resin; a polycarbonate resin; a polyphenylene sulfide resin; a polysulfone resin; a fluorine resin; a silicone resin; a urea resin; a melamine resin; a guanamine resin; a phenol resin; a cellulose resin; and a combination of the above-described resins. That is, the "hydrophobicity" in the present specification means that the contact angle measured in accordance with the sessile drop method regulated in JIS R3257-1999 is greater than or equal to 70 degrees.

Both the hydrophilic resin and the hydrophobic resin may be a thermoplastic resin or a thermosetting resin. Further, it may be a resin which is cured using an active energy ray such as an electron beam or UV light, or may be an elastomer.

Use of a photoresist as a resin material can accurately form a large number of fine through-holes in the wall layer 32 through photolithography.

In the case of using photolithography, it is possible to appropriately select well-known means for a method for selecting the type of photoresist to be used, a coating method, an exposing method, and a method for removing an unnecessary photoresist.

In a case where the resist is not used, the wall layer 32 can be formed through, for example, injection molding.

As the colored component, an organic or inorganic pigment is an exemplary example. Specific examples of black pigments include carbon black, acetylene black, and iron black. Examples of yellow pigments include chromium yellow, zinc yellow, ocher, Hansa yellow, permanent yellow, and benzine yellow. Examples of orange pigments include orange lake, molybdenum orange, and benzine orange. Examples of red pigments include red iron oxide, cadmium red, antimony vermilion, permanent red, lithol red, lake red, brilliant scarlet, and thioindigo red. Examples of blue pigments include ultramarine, cobalt blue, phthalocyanine blue, Ferrocyanide blue, and indigo. Examples of green pigments include chrome green, viridian naphthol green, and phthalocyanine green.

In addition, in a case where the wall layer 32 is formed through injection molding or the like, not only pigments dispersed in a resin but also various dyes soluble in a resin can be used as colored components. Exemplary examples of dyes can be produced by various dyeing methods. Specific examples thereof include direct dyes, basic dyes, cationic dyes, acidic dyes, mordant dyes, acidic mordant dyes, sulfur dyes, vat dyes, naphthol dyes, disperse dyes, and reactive dyes. Particularly, in a case of dyeing a resin, in many cases, disperse dyes are often selected.

In the present specification, a microwell means a well having a volume of less than or equal to 10 nanoliters (nL). By making the volume of the microwells 33 as small as this, it is possible to suitably perform an enzymatic reaction, such as digital PCR and an invader reaction, carried out in a minute space. For example, gene mutation detection and the like can be performed through digital PCR.

The volume of the microwells 33 is preferably 1 femtoliter (fL) to 6 nL, more preferably 1 fL to 5 picoliters (pL), and most preferably 1 fL to 300 fL. In a case where the volume is set within such a range, it is possible to accommodate only one to several biomolecules or carriers in one microwell 33 during sample analysis to be described below.

The shapes of the microwells 33 are not particularly limited as long as the volume is within the above-described range. Accordingly, it is possible to use, for example, a cylindrical shape, a polyhedron (for example, a rectangular parallelepiped, a hexagonal prism, and an octagonal prism) formed by a plurality of surfaces, an inverted conical shape, and an inverted pyramidal shape (an inverted triangular pyramidal shape, an inverted quadrangular pyramidal shape, an inverted pentagonal pyramidal shape, an inverted hexagonal pyramidal shape, and an inverted heptagonal or higher polygonal pyramidal shape).

Furthermore, a shape combining two or more of the above-described shapes may be used. For example, some microwells may have a cylindrical shape and the remaining microwells may have an inverted conical shape. In addition, in the case of an inverted conical shape or an inverted pyramidal shape, the bottom surface of a cone or a pyramid is an opening portion that communicates a flow path with the microwells 33. In this case, the bottom portions of the microwells 33 may be made flat using a shape obtained by cutting a part from the top of an inverted conical shape or inverted pyramidal shape. As another example, the bottom portions may be formed into curved surface shapes that protrudes or recesses toward the opening portion.

The thickness of the wall layer 32 defines the depth of the microwells 33. In a case where the microwells are cylindrical, the thickness of the wall layer 32 can be set to be within a range of, for example, 10 nm to 100 µm, preferably 100 nm to 10 µm, and more preferably 1 µm to 10 µm for the purpose of sealing an aqueous liquid (sample) containing biomolecules.

The dimensions of each part of the microwells 33 may be appropriately determined so that one or several molecules are accommodated in one microwell in consideration of the amount of aqueous liquid to be accommodated, the sizes of carriers such as beads to which biomolecules are attached, and the like.

The number and the density of the microwells 33 provided in the microwell array 30 can be appropriately set.

The number of microwells 33 per 1 cm2 is, for example, 10,000 to 10,000,000, preferably 100,000 to 5,000,000, and more preferably 100,000 to 1,000,000. In a case where the density of the microwells is within this range, an operation of sealing an aqueous liquid as a sample in a predetermined number of wells is facilitated. In addition, it is easy to observe wells for analyzing experimental results. For example, when measuring mutation of cell-free DNA, in a case where the proportion of the mutation to be detected relative to a wild type is about 0.01%, it is suitable to use, for example, about 1,000,000 to 2,000,000 microwells.

FIG. 1 shows an example of a one-dimensional array in which a plurality of microwells 33 are arranged in a line. However, in a case of providing a large number of microwells as described above, a two-dimensional array in which a plurality of microwells are two-dimensionally arranged may be used.

In a case where pigments are used as colored components, the particle diameters of the pigments are set within a predetermined range according to the sizes of the microwells. If particle diameter of a pigment is smaller than or equal to one fifth of a smaller dimension between the dimension in a radial direction and the dimension in a depth direction of microwells (hereinafter referred to as a "minimum dimension"), the accuracy in forming the microwells is not affected. It is more preferable to set the particle diameters to be smaller than or equal to one tenth of the minimum dimension. For example, in a case where the minimum dimension is about 10 nm to 100 µm, the particle diameters of pigments are preferably about 1 nm to 10 µm. In a case where the minimum dimension is 100 nm to 10 µm, the particle diameters of pigments are preferably about 10 nm to 1 µm in manufacturer's catalog values or the like.

By setting the particle diameters of pigments within the above-described range, the sizes of pigments become sufficiently small with respect to the microwells. As a result, even when forming a large number of microwells, it is possible to accurately form the microwells without being interrupted by the particles of the pigments. In addition, by making an uncolored region between the particles of the pigments sufficiently small with respect to the microwells, it is possible to suitably exhibit an effect of suppressing autofluorescence described below.

A peripheral member 34 having a frame shape in plan view is disposed around the microwell array. The dimension of the peripheral member 34 in the thickness direction of the microfluidic device 1 is larger than that of the wall layer 32. The peripheral member 34 supports the lid member 20 to secure a gap between the lid member 20 and the microwell array and maintain the flow path.

The material or the like of the peripheral member 34 is not particularly limited, and examples thereof include a silicone rubber and a double-sided adhesive tape having an acrylic adhesive stacked on both sides of a core material film formed of an acrylic foamed body.

The microfluidic device 1 formed as described above can be manufactured, for example, through the following procedure.

First, the base plate 10 is prepared and a resin layer for a wall portion which becomes the wall layer 32 is formed on the surface of the base plate 10. In a case where the bottom layer 31 is provided, the bottom layer 31 is formed before the formation of the resin layer for a wall portion. Even in a case where the bottom layer 31 is not provided, an anchor layer or the like for enhancing adhesiveness between the base plate 10 and the resin layer for a wall portion may be provided on the surface of the base plate 10 as necessary.

The resin layer for a wall portion is formed of a material obtained by mixing a colored component with a resin material. In a case where the resin material is a resist, the content ratio of the colored component can be set to, for example, 0.5 mass % (wt %) to 60 wt %. The content ratio is preferably 5 wt % to 55 wt % and more preferably 20 wt % to 50 wt %. The content ratio of the colored component can be appropriately set so that a desired pattern can be formed in consideration of the proportion of a photosensitive component and the like contained in the resist. In a case where the colored component is a pigment, the particle diameter of the pigment is set and prepared so as to satisfy the above-described predetermined conditions with respect to microwells to be formed. A dispersant may be appropriately added together with the pigment.

The formed resin layer for a wall portion has a color based on a colored component contained therein.

Next, a through-hole 32a is formed in the formed resin layer for a wall portion. As described above, it is possible to simply form the through-hole 32a accurately through photolithography. In a case where the resin layer for a wall portion is formed through injection molding or the like, formation of the resin layer for a wall portion and formation of the through-hole can be performed through the same process. In addition, it is possible to form the through-hole 32a also through etching or the like using a pattern mask.

After the through-hole 32a is formed, the resin layer for a wall portion becomes the wall layer 32, and the microwell array 30 is completed.

Thereafter, the peripheral member 34 is disposed around the microwell array 30, and then, the lid member 20 is disposed on the peripheral member 34. Once the base plate 10, the peripheral member 34, and the lid member 20 are integrally joined to each other, the microfluidic device 1 is completed.

Next, a sample analysis method of the present embodiment using the microfluidic device 1 according to the present embodiment will be described.

In the microwell array 30 of the present embodiment, it is significantly easy to seal an aqueous liquid such as a sample in each microwell 33. Here, sealing means that an aqueous liquid is introduced into each of the microwells 33 of the microwell array 30, and that the liquids introduced into the respective wells are separated from each other in a state in which the liquids are not mixed with each other. Examples of the separation method include a method for introducing an aqueous liquid into a well, followed by filling the flow path with a sealing liquid to be described below. According to the microfluidic device 1 of the present embodiment, it is possible to easily seal an aqueous liquid in at least greater than or equal to 90% of the microwells, for example, greater than or equal to 95% of the microwells, greater than or equal to 99% of the microwells, or 100% of the microwells.

In the microwell array of the present embodiment, even in a case where the temperature of a sealed aqueous liquid is changed, for example, in gene mutation detection or the like, the aqueous liquid can be suitably held in the wells. The range of the temperature to be changed is, for example, 0° C. to 100° C., preferably 0° C. to 80° C., and more preferably 20° C. to 70° C. In a case where the temperature of the aqueous solution sealed in the wells is within this range, it is possible to suitably perform an enzymatic reaction, such as digital PCR or an invader reaction, carried out in a minute space.

An example of a sample to be analyzed using the microfluidic device 1 according to the present embodiment includes a sample collected from a living body such as blood. In addition, a detection target to be detected through sample analysis may be a PCR product or the like, or may be an artificially synthesized compound or the like. For example, in a case where DNA which is a biomolecule is to be detected, each well may have a shape and a size so as to contain one molecule of DNA.

Hereinafter, the details of the sample analysis method will be described while taking a case of fluorescence observation using a fluorescence microscope as an example. As a preparation step, a sample to be sealed in the microwells is prepared. The sample is an aqueous liquid containing a detection target, and an example thereof includes a PCR reaction solution containing SYBR Green as a detection reagent using a biological sample as a template. For adjustment, a surfactant may be added thereto to make the sample more easily enter the microwells. In addition, beads that specifically recognize the detection target may be added thereto to capture the detection target.

Figure 3:
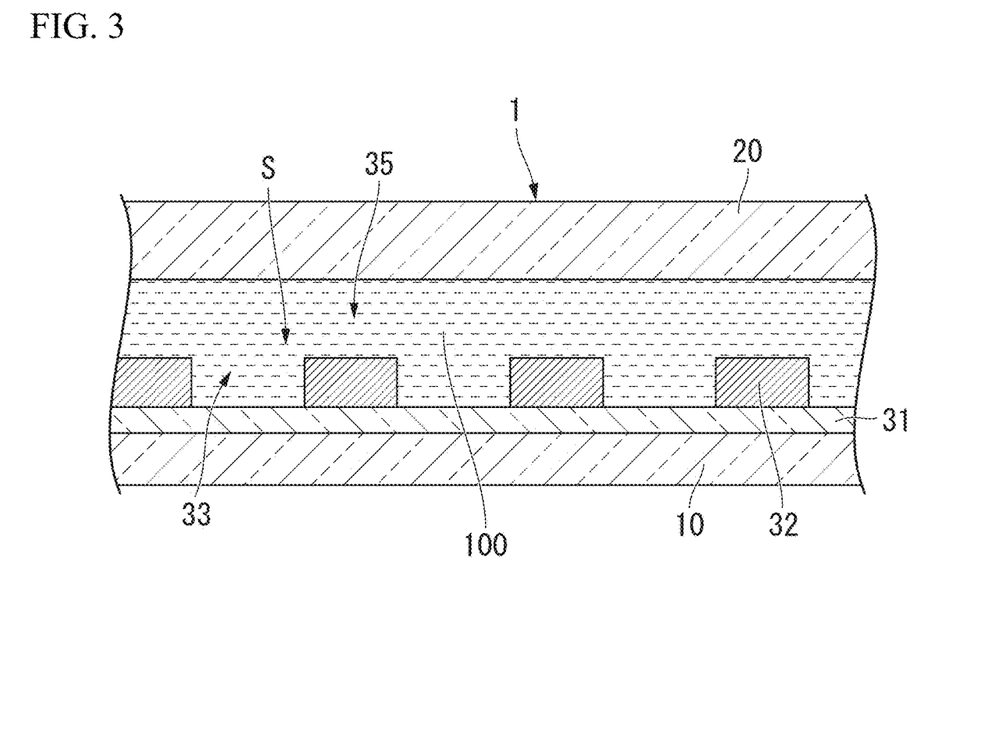
FIG. 3 is a view showing a state in use of the microfluidic device according to the embodiment of the present invention.

Next, the prepared sample is supplied from the first hole 21 to the internal space S using a syringe or the like (sample supply step). As shown in FIG. 3, each microwell 33 and a flow path 35 are filled with the supplied sample 100. Gas in the internal space S is removed in advance before the sample supply step. This deaeration operation may be performed by filling the internal space S with a buffer.

Next, a sealing step of sealing the sample in the microwells 33 is performed. Before the sealing step, a fluorescent label is attached to the detection target in the sample. The fluorescent labeling treatment may be performed before the sample supply step, for example, at the time of preparation of the sample, or may be performed by introducing the fluorescent label into the internal space S after the sample supply step.

Figure 4:
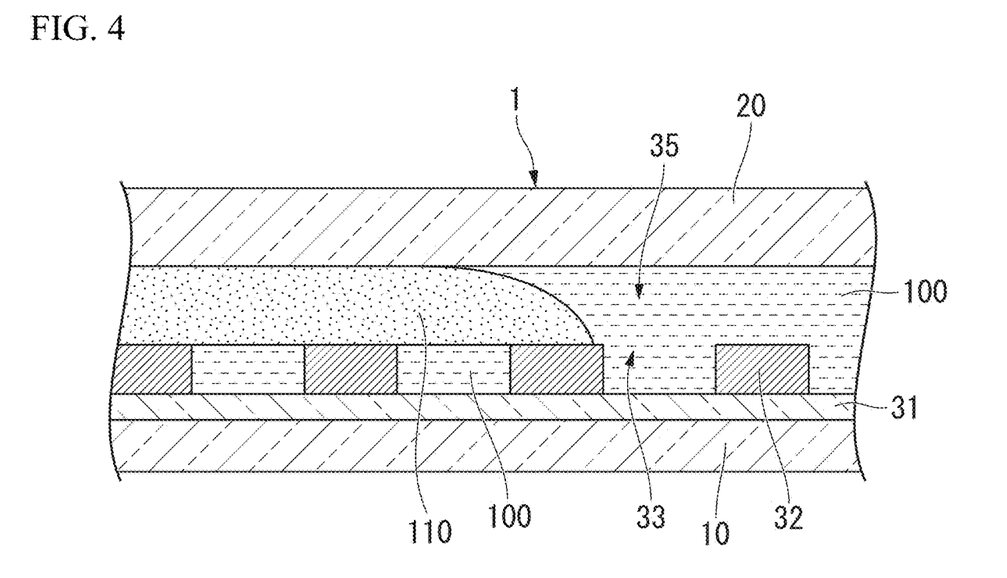
FIG. 4 is a view showing a state in use of the microfluidic device according to the embodiment of the present invention.

In the sealing step, a sealing liquid is supplied from the first hole 21 to the internal space S using a syringe or the like (sample supply step). The supplied sealing liquid 110 flows through the flow path and is replaced with the sample 100 existing in the flow path 35 as shown in FIG. 4. As a result, the sample 100 is disposed in each microwell 33 in a mutually independent state, and the sealing of the sample is completed.

In the present specification, the sealing liquid means a liquid used for separating aqueous liquids introduced into each microwell 33 of the microwell array 30 from each other in a state in which the aqueous liquids are not mixed with each other, and examples thereof include oils and the like. It is possible to use, for example, "FC 40" which is a trade name and manufactured by Sigma Corporation or "HFE-7500" which is a trade name and manufactured by 3M, and mineral oil used for a PCR reaction and the like, as the oils.

It is preferable that the sealing liquid has a contact angle of 5 degrees to 80 degrees with respect to the material of the wall layer 32. In a case where the contact angle of the sealing liquid is within this range, it is possible to suitably seal the sample in each microwell 33. The contact angle of the sealing liquid may be measured using a sealing liquid instead of water in accordance with, for example, the sessile drop method defined in JIS R3257-1999.

Subsequently, fluorescence observation of the sample is performed. However, the microfluidic device may be subjected to a thermal cycler and an enzymatic reaction such as a PCR reaction or an invader reaction may be performed as necessary before the fluorescence observation.

Next, the microfluidic device 1 after the sealing step is set on an inverted fluorescence microscope with the base plate 10 placed on a lower side, and excitation light (electromagnetic wave) is radiated from the base plate 10 side (electromagnetic wave irradiation step). The wavelength of the excitation light is appropriately set according to the fluorescent label used.

In a case where the fluorescence-labeled detection target is sealed in the microwells 33, the microwells emit fluorescence due to the excitation light. A user observes a well that emits fluorescence from the base plate 10 side with a microscope (sample observation step). In a case where the detection target is, for example, a single nucleotide polymorphism (SNP), it is possible to analyze SNP expression frequency and the like by counting the number of microwells emitting fluorescence.

In the microfluidic device 1 according to the present embodiment, the wall layer 32 constituting the wall surface of the microwell array is formed of a material containing a colored component. Accordingly, even if the resin material of the wall layer 32 has autofluorescence with respect to the excitation light, the generated autofluorescence is absorbed and canceled out by the colored component, and the autofluorescence is reduced. As a result, autofluorescence around the microwells 33 is suitably reduced, and interference of the observation of the microwells 33 is suitably prevented.

In addition, the particle diameter of the colored component is within a predetermined range with respect to the minimum dimension of the microwells 33. For this reason, it is possible to reduce the influence of autofluorescence in sample analysis while suppressing the influence on the accuracy in forming the microwells 33.

Furthermore, the particles of the colored component moderately roughen the inner wall surfaces of the microwells 33. As a result, the contact area between the sample and the microwells is increases, and the sealing efficiency can be improved.

Furthermore, even in a case where a substance (for example, dust) other than a resin which has autofluorescence is contained in the material of forming the wall layer 32, since the colored component exists around the substance, the excitation light hardly reaches the substance. Even if a small amount of excitation light reaches the substance, the generated autofluorescence is absorbed and canceled out by the colored component. Therefore, the excitation light hardly affects the sample analysis.

In addition, since it is easy to recognize the position of the boundary between the base plate 10 and the wall layer 32, it is easy to focus the microscope near the bottom surfaces of the microwells 33 in the sample observation step. Accordingly, sample observation can be easily and suitably performed.

Furthermore, since the wall layer 32 is colored, visibility of the wall layer 32 is improved. Therefore, it is possible to suitably confirm the formation condition and the like. Accordingly, quality check such as quality control or process control in the manufacture of the microfluidic device 1 becomes easy.

Furthermore, it is possible to prevent forgery using the color characteristics of the wall layer 32. In a case where the wall layer is transparent, it is impossible to determine whether or not it is made of a predetermined resin only by the appearance. As in the present embodiment, in a case where a wall layer is made of a material containing a colored component such as Ferrocyanide blue, it is possible to easily distinguish between a product manufactured by a rightful manufacturer and a forgery manufactured by a third party using an absorption spectrum measured with a spectrophotometer even if the wall layers have a similar color at a glance.

In addition, according to the sample analysis method of the present embodiment, the microfluidic device 1 is irradiated with an electromagnetic wave in the electromagnetic wave irradiation step, and the sample in the microwells 33 irradiated with the electromagnetic wave is observed from the base plate 10 side. Accordingly, the following effects are exhibited.

Figure 5:
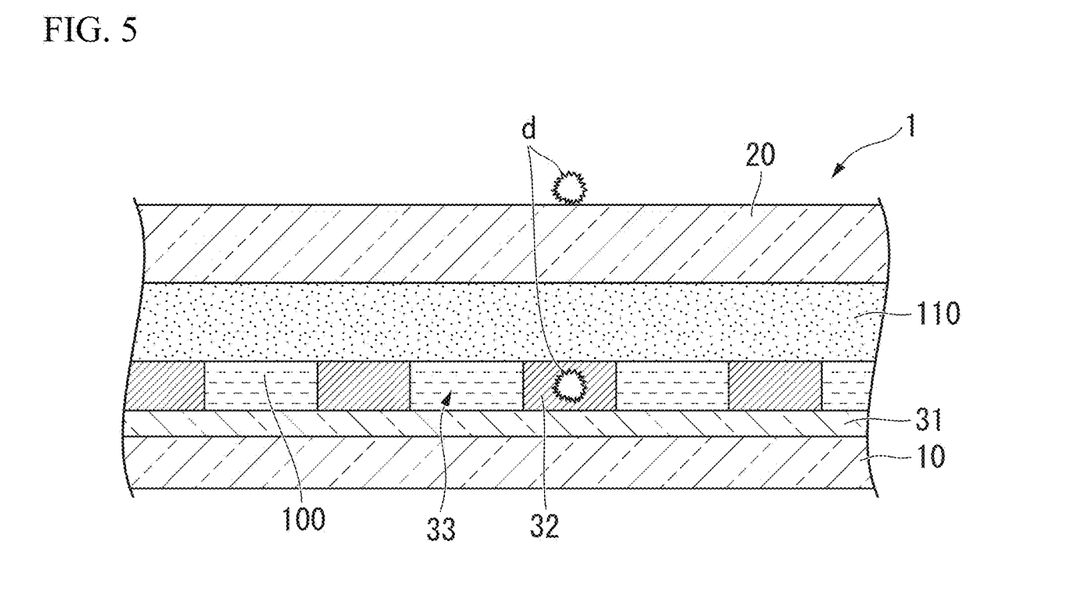
FIG. 5 is a view showing an effect of a sample analysis method in which the microfluidic device according to the embodiment of the present invention is used.

As shown in FIG. 5, in a case where dust d having autofluorescence falls on the lid member 20 of the microfluidic device 1, the dust d emits fluorescence due to the irradiated excitation light. In the analysis of the microwells 33, there is a sufficient possibility that even the fluorescence emitted by a small object such as dust d becomes a noise that interferes with the sample analysis. In the sample analysis method according to the present embodiment, the microwells 33 are observed from the base plate 10 side. For this reason, even if the dust d falling to the position overlapping the wall layer 32 in the plan view of the microfluidic device 1 emits fluorescence, it is suitably canceled out by the colored component of the wall layer 32. In addition, in a case where the excitation light is radiated from the base plate 10 side, the excitation light reaching the dust d decreases due to the colored component of the wall layer 32. Therefore, the fluorescence itself is hardly generated. Accordingly, sample analysis can be performed while suitably suppressing the influence of autofluorescence caused by factors other than the material forming the wall layer 32.

Furthermore, even in a case where the autofluorescent foreign matter such as dust d is present in the wall layer 32, in most cases, the material for forming the wall layer 32 containing a colored component is present between the autofluorescent foreign matter and the base plate 10. For this reason, the colored component suppresses the generation of autofluorescence, and the generated fluorescence is also absorbed by the colored component and suitably canceled out. In a case where the autofluorescent foreign matter is fibrous, the colored component penetrates the foreign matter and more suitably absorbs the autofluorescence.

In the present embodiment, the fluorescence wavelength to be used can be selected at an arbitrary wavelength. For example, in a case where fluorescence having a peak in a wavelength range of 350 to 700 nm which is a visible light region is detected, colors of fluorescent molecules to be bonded are made to be different from each other for each biomolecule to be detected, by selecting blue, green, yellow, red, or the like as the color of fluorescence to be generated. Accordingly, it possible to detect a plurality of kinds of biomolecules through one detection.

Here, in a case where a black or blue component is used as a colored component, electromagnetic waves in a wide wavelength range can be absorbed, which is preferable because of high versatility.

In addition, the electromagnetic wave absorption characteristics of the colored component may be appropriately changed according to the fluorescence wavelength to be used, the wavelength of excitation light to be used, and the autofluorescence wavelength of dust or the like which may possibly fall. In addition, the wall layer does not necessarily have to completely absorb the electromagnetic waves of a predetermined wavelength, and it is sufficient that it is possible to reduce the influence of the above-described autofluorescence to a degree that no problem occurs in sample analysis. The "degree that no problem occurs in sample analysis" is at least less than or equal to one half of the fluorescence intensity of a detection target, and more preferably less than or equal to one tenth of the fluorescence intensity of a detection target.

The microfluidic device and the sample analysis method according to the present embodiment described above will be further described using Examples and Comparative Examples for checking effects.

Example 1

A glass base plate having a thickness of 500 μm was prepared as the base plate 10 having no autofluorescence. A solution containing hexamethyldisilazane (HMDS) was applied to one surface of the base plate 10 to form the bottom layer 31.

A material obtained by adding 30 wt % of Ferrocyanide blue to a negative type photoresist cured through exposure was used as a material for forming the wall layer 32. The forming material was applied to the bottom layer 31 through spin coating in a thickness of 3 μm. The forming material was pre-baked, and was then exposed. Next, the wall layer 32 was formed by performing developing process and removing the unnecessary photoresist.

The pre-baking conditions, the exposure conditions, and the like were appropriately set based on the photoresist used.

As a result, a laminate of Example 1 having the same layer structure as that of the microfluidic device according to the present embodiment was obtained.

Example 2

A glass base plate having a thickness of 500 μm was prepared as the base plate 10 having no autofluorescence. A solution containing hexamethyldisilazane (HMDS) was applied to one surface of the base plate 10 to form the bottom layer 31.

A material obtained by adding 30 wt % of Ferrocyanide blue to a negative type photoresist cured through exposure was used as a material for forming the wall layer 32. The forming material was applied to the bottom layer 31 through spin coating in a thickness of 3 μm and was pre-baked. Thereafter, the forming material was exposed so as to form a minute hole (through-hole) in a dot shape. Next, development processing was performed to remove the unnecessary photoresist. In this manner, the wall layer 32 having a minute hole was formed.

The pre-baking conditions, the exposure conditions, and the like were appropriately set based on the photoresist used.

As a result, a laminate of Example 2 having the same layer structure as that of the microfluidic device according to the present embodiment was obtained.

Comparative Example 1

The same glass base plate as that in Example 1 was prepared as a base plate. A thermosetting resin (CYTOP manufactured by Asahi Glass Co., Ltd.) which was transparent and colorless and did not have autofluorescence was applied to one surface of the base plate through spin coating in a thickness of 3 µm. The thermosetting resin was baked and cured to form a wall layer.

As a result, a laminate of Comparative Example 1 in which the wall layer did not contain a colored component was obtained.

Comparative Example 2

The same glass base plate as that in Example 1 was prepared as a base plate. A thermosetting resin (CYTOP manufactured by Asahi Glass Co., Ltd.) which was transparent and colorless and did not have autofluorescence was applied to one surface of the base plate through spin coating in a thickness of 3 µm. The thermosetting resin was baked and cured. A resist for dry etching was applied thereon, and was exposed so as to form a minute hole (through-hole) in a dot shape. Next, development processing was performed to remove the unnecessary resist. Accordingly, a photoresist for dry etching was formed on CYTOP. Dry etching was performed on the photoresist to form a wall layer formed of CYTOP. Finally, the photoresist for dry etching on CYTOP was removed, and minute holes (through-holes) were formed in the wall layer.

As a result, a laminate of Comparative Example 2 in which the wall layer did not contain a colored component was obtained.

(Observation Procedure Using Example 1 and Comparative Example 1)

Light beams having three kinds of wavelengths of 350 nm, 480 nm, and 590 nm were used as excitation light beams. Sheets having autofluorescence for all the excitation light beams were disposed in contact with the wall layers 32 of Example 1 and Comparative Example 1. Thereafter, each excitation light beam was radiated from the base plate 10 side, and the fluorescence intensity of fluorescence returning to the base plate 10 side was measured.

(Result)

Figure 6:
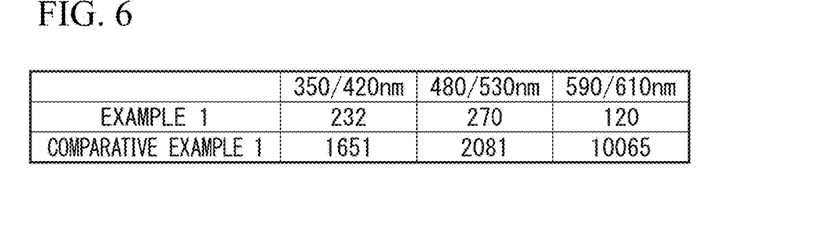
FIG. 6 is a table showing experimental results regarding effects of microfluidic devices using Example 1 and Comparative Example 1

The measurement results of Example 1 and Comparative Example 1 are shown in FIG. 6. The fluorescence wavelength is shown alongside the wavelength of each excitation light beam.

The fluorescence intensity was measured under the same conditions for excitation light of each wavelength used. As a result, it was confirmed that the fluorescence intensity can be further reduced to about one seventh to one eightieth which did not cause a problem in sample analysis in Example 1 compared to Comparative Example 1.

Figure 7:
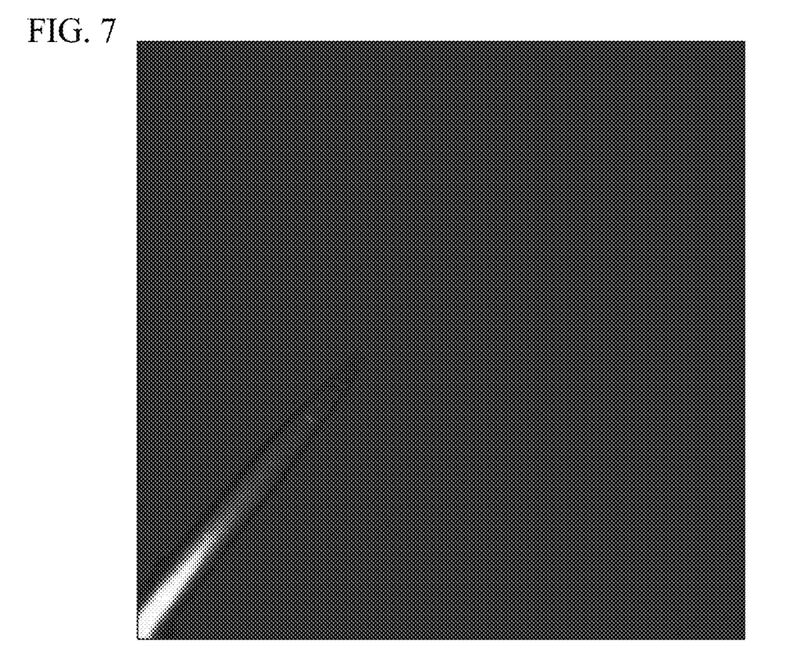
FIG. 7 is a microscopic image of Example 1.

FIG. 7 shows a microscopic image of Example 1. In a lower left partial region of the image, the wall layer 32 has been removed for comparison. Only the partial region appears bright with the fluorescence of the autofluorescent sheet. However, the other part is dark, and the wall layer 32 suitably reduces the influence of the fluorescence of the autofluorescent sheet.

Figure 8:
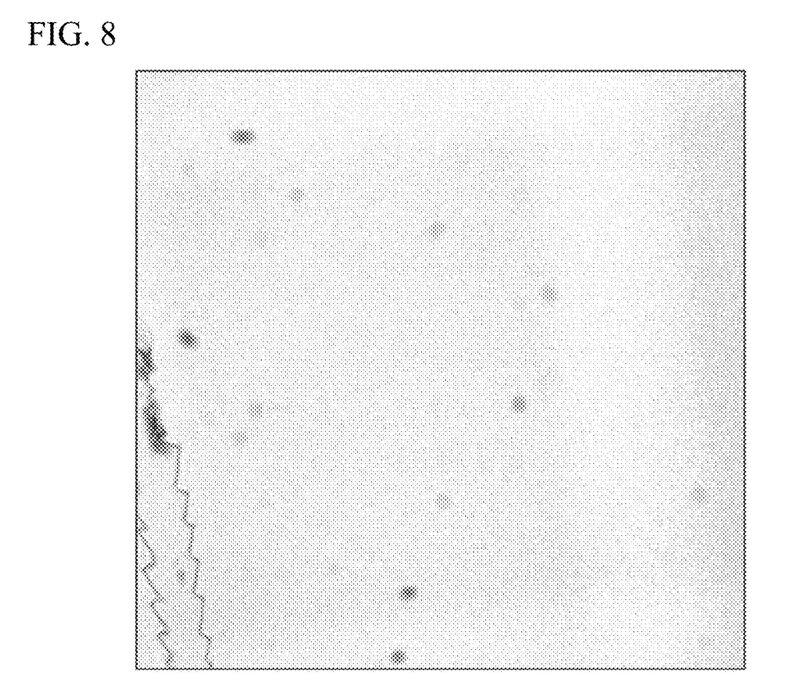
FIG. 8 is a microscopic image of Comparative Example 1.

FIG. 8 shows a microscopic image of Comparative Example 1. In a lower left band-like portion, the wall layer has been removed in the same manner as in FIG. 7. In Comparative Example 1, the whole body appears bright regardless of the presence or absence of the wall layer. This shows that the autofluorescence strongly affects the brightness.

Figure 9:
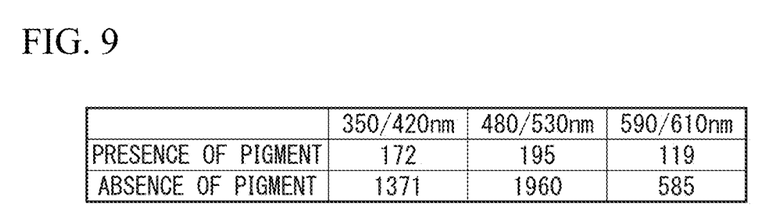
FIG. 9 is a table showing the difference in fluorescence intensity depending on the presence or absence of a pigment in the material used in Example 1.

The photoresist itself used as the material of the wall layer 32 has autofluorescence with respect to the excitation light beams of the above-described wavelengths. FIG. 9 shows the difference in fluorescence intensity of the photoresist depending on the presence or absence of a pigment. The data of "no pigment" was obtained by setting the measurement conditions such as the thickness and the fluorescence intensity of the photoresist in the same manner as in Example 1.

As shown in FIG. 9, the photoresist shows strong autofluorescence in a state where no pigment has been added. Accordingly, it is shown that even a material having autofluorescence with respect to an excitation wavelength to be used can be used as a material for the wall layer when the material contains a colored component.

(Observation Procedure Using Example 2 and Comparative Example 2)

Light beams having a wavelength of 488 nm were used as excitation light beams. Sheets having autofluorescence for all the excitation light beams were disposed in contact with the wall layer 32 of Example 2 and Comparative Example 2. Thereafter, each excitation light beam was radiated from the base plate 10 side, and the fluorescence intensity of fluorescence returning to the base plate 10 side was measured.

(Result)

The fluorescence intensity was measured under the same conditions for the excitation light beams used in Example 2 and Comparative Example 2. As a result, in Example 2, fluorescence was observed only in the minute hole portion (of which the bottom surface was made of glass and transparent) with respect to Comparative Example 2. In Comparative Example 2, fluorescence was observed not only in the minute hole portion but also in the portion having the wall layer.

Figure 11A:
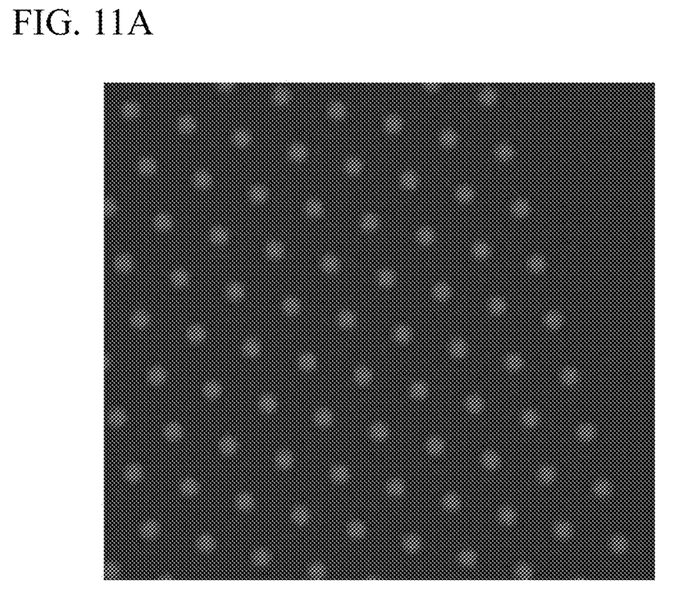
FIG. 11A is a result of bright field observation of Example 2.
Figure 11B:
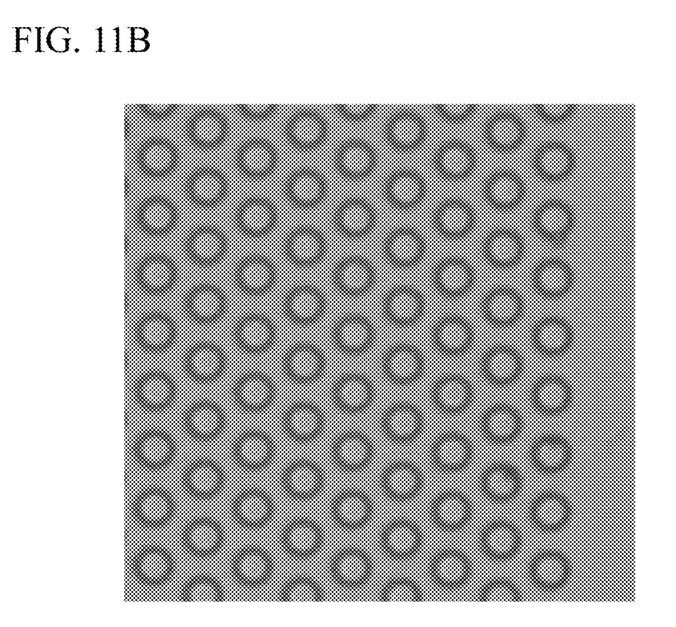
FIG. 11B is a result of bright field observation of Comparative Example 2.

The results of bright field observation of Example 2 and Comparative Example 2 are shown in FIGS. 11A and 11B. In Example 2, portions other than the minute holes were colored and appeared dark (the minute hole portions were transparent because the bottoms of the minute hole portions were made of glass).

Figure 12:
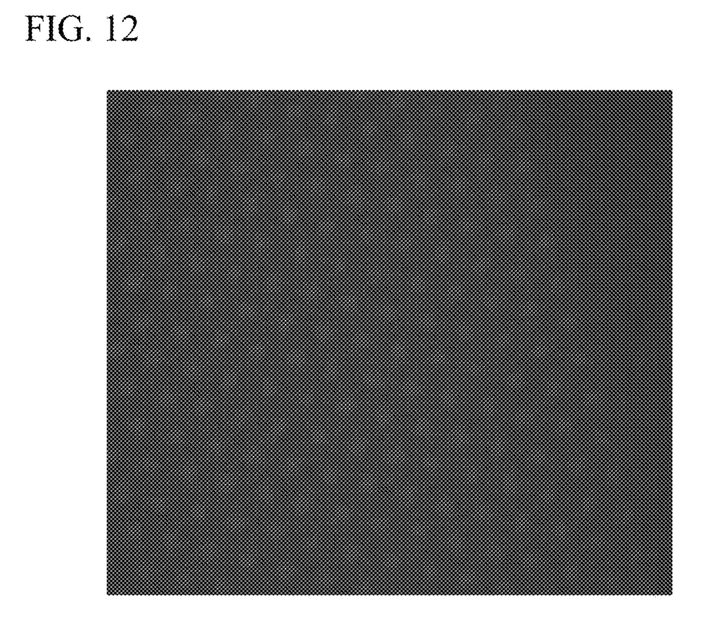
FIG. 12 is a microscopic image of Example 2.

FIG. 12 shows a microscopic image of Example 2. No wall layer 32 was observed in a region observed in a dot shape in the image. Only the portion of the minute holes appeared bright, but the other portion was dark. Accordingly, it was confirmed that the wall layer 32 suitably reduced the influence of the fluorescence of the autofluorescent sheet.

Figure 13:
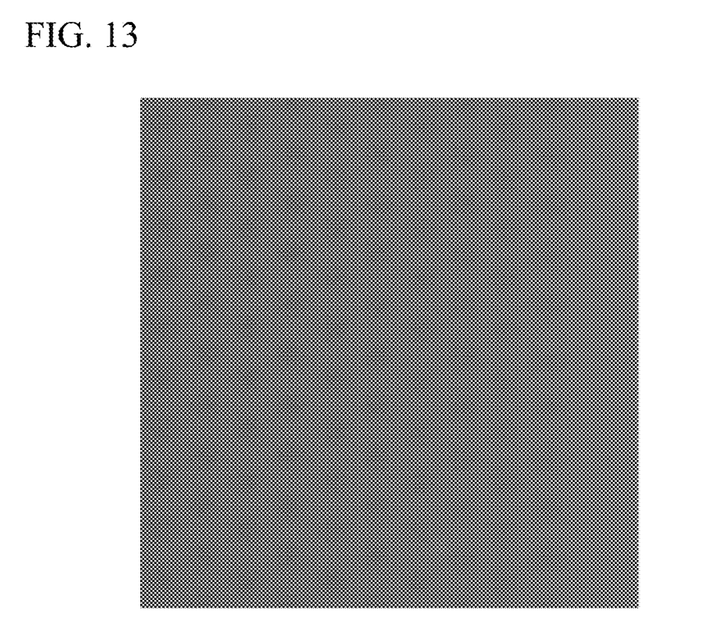
FIG. 13 is a microscopic image of Comparative Example 2.

FIG. 13 shows a microscopic image of Comparative Example 2. As can be seen from the bright field image in FIG. 11B, there are dot-shaped minute holes. However, in Comparative Example 2, the entirety appears bright regardless of the presence or absence of the wall layer. This shows that the autofluorescence strongly affects the brightness.

The microfluidic device and the sample analysis method according to an embodiment of the present invention have been described using the embodiment and Examples. However, the technical scope of the present invention is not limited to the above-described embodiment and Examples, and it is possible to change the combination of constituent elements within the scope not departing from the gist of the present invention, to make various changes in each constituent element, or to delete the constituent elements.

For example, in the sample analysis method according to the present embodiment, in a case where the base plate of the microfluidic device is disposed on the lower side as described above, dust or the like is less likely to fall on the base plate, which is preferable. However, the sample observation step may be performed in a state where the base plate is disposed on an upper side. Even in this case, it is possible to reduce autofluorescence in a case where a foreign matter such as dust having autofluorescence adheres to the lid member 20.

However, in the case of disposing the base plate on the upper side, if dust or the like falls on the base plate, there is a possibility that autofluorescence such as dust may affect the sample observation. Therefore, it is preferable to perform processing such as jetting of air onto the base plate immediately before the sample observation step.

Figure 10:
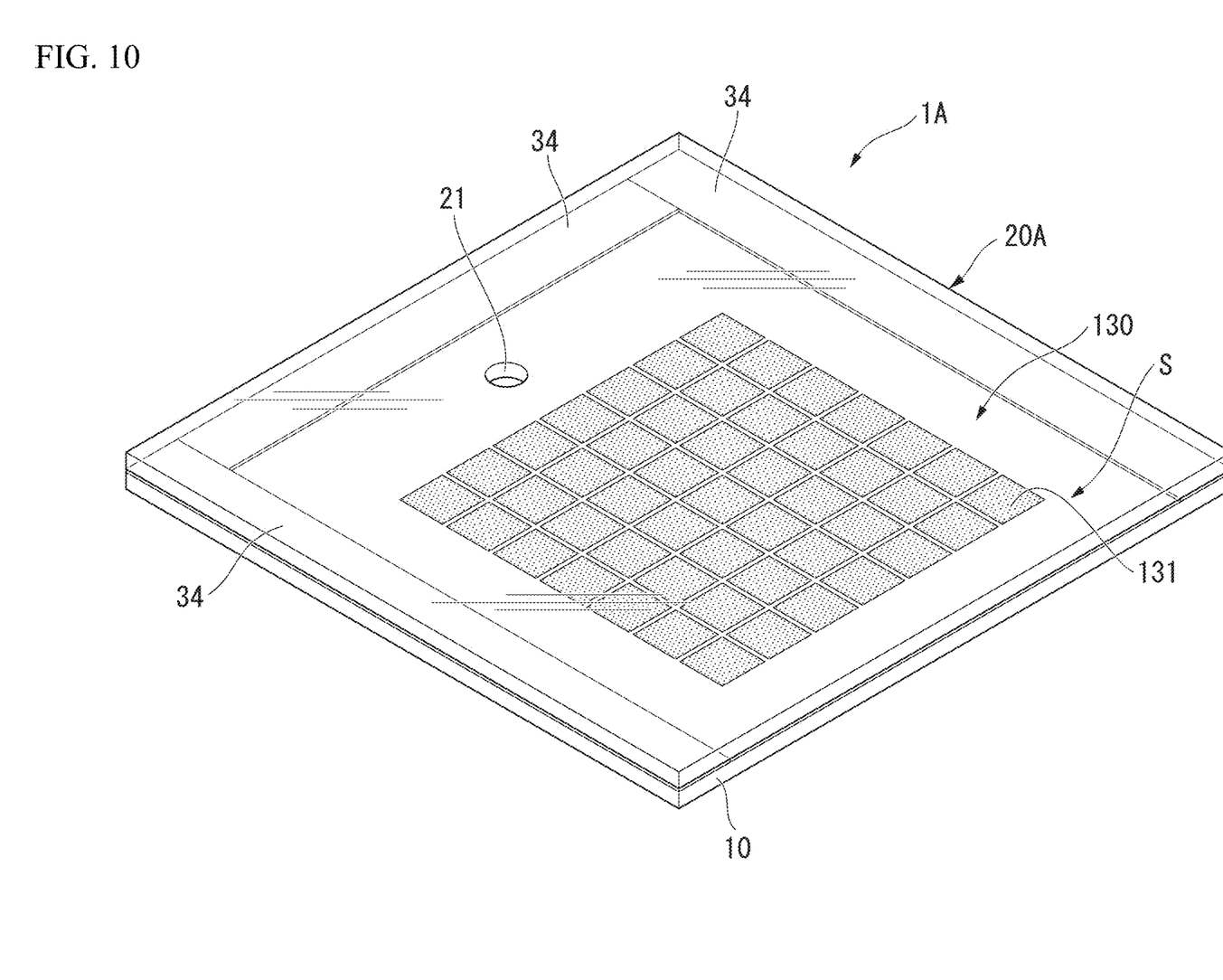
FIG. 10 is a perspective view showing a modification example of the microfluidic device according to the embodiment of the present invention.

In addition, a microfluidic device 1A in which microwells are arranged in a two-dimensional array shape is shown in FIG. 10 as a modification example of the microfluidic device according to the present embodiment. Components common to the microfluidic device 1 are denoted by the same reference numerals, and redundant descriptions will not be repeated.

In the microfluidic device 1A, unit well arrays 131 in which microwells (not shown in the drawing) are arranged in a two-dimensional array shape are further arranged in a two-dimensional array to form a microwell array 130. In this manner, a large number of microwells can be arranged with high accuracy and high density.

A lid member 20A of the microfluidic device 1A does not have a second hole. Instead, a part of the peripheral edge of an internal space S is opened by not disposing a peripheral member 34 on one side of the rectangular shape in plan view of the microfluidic device 1A. Accordingly, an excess portion of a sample introduced from a first hole 21 or a sealing liquid is discharged from the open peripheral edge. Even if the microfluidic device is formed in this manner, the same effect is exhibited.

In addition, the sample analysis method according to the present embodiment is not limited to a method using fluorescence or phosphorescence. For example, the method can also be applied to sample analysis using turbidity or the like. In a case where turbidity is used, it is possible to perform measurement using light having a wavelength of, for example, about 400 to 1,000 nm, and the electromagnetic wave absorption characteristics of the colored component and the wall layer may be set based on the measurement.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

DESCRIPTION OF REFERENCE NUMERAL 1, 1A: microfluidic device
10: base plate
20, 20A: lid member
30: microwell array
32: wall layer
33: microwell
100: sample
110: sealing liquid

What is claimed is:

1. A microfluidic device comprising:
a base plate having a first composition and allowing an electromagnetic wave having a wavelength to pass through the base plate, the based plate including a material suppressing auto-fluorescence from excitation by the electromagnetic wave having the wavelength;
a microwell array formed on the base plate and including a wall layer, the wall layer including a plurality of through-holes formed in a thickness direction of the wall layer to form microwells; and
a lid member disposed over an opposite side of the microwell array opposite to a base plate side of the microwell array facing the base plate, the lid member disposed to be in a state of being separated from the wall layer, wherein
bottoms of the microwells are constituted by the base plate,
sidewalls of the microwells are constituted by the wall layer,
the microwells are open toward the lid member,
the through-holes as the microwells are configured to hold a reagent, and
the wall layer having a second composition different from the first composition, the wall layer having the second composition including a resin and a particle-shaped component which absorbs an electromagnetic wave of a same wavelength as a fluorescence wavelength of a fluorescence emitted from the reagent.

2. The microfluidic device according to claim 1, wherein a particle diameter of the particle-shaped component is less than or equal to one fifth of a minimum dimension of each microwell of the microwells.

3. A sample analysis method in which the microfluidic device according to claim 1 is used, the method comprising:
supplying a sample into each of the microwells;
sealing the sample in each of the microwells using a sealing liquid;
irradiating the microfluidic device with an electromagnetic wave after sealing the sample in each of the microwells; and
observing, from the base plate side, the microwells irradiated with the electromagnetic wave.

4. A sample analysis method in which the microfluidic device according to claim 2 is used, the method comprising:
supplying a sample into each of the microwells;
sealing the sample in each of the microwells using a sealing liquid;
irradiating the microfluidic device with an electromagnetic wave after sealing the sample in each of the microwells; and
observing, from the base plate side, the microwells irradiated with the electromagnetic wave.

5. The microfluidic device according to claim 4, wherein the particle-shaped component includes one of carbon black, acetylene black, iron black, chromium yellow, zinc yellow, ocher, Hansa yellow, permanent yellow, benzene yellow, orange lake, molybdenum orange, benzene orange, red iron oxide, cadmium red, antimony vermilion, permanent red, lithol red, lake red, brilliant scarlet, thioindigo red, ultramarine, cobalt blue, phtalocyanine blue, Ferrocyanide blue, indigo, chrome green, viridian naphthol green, and phthalocyanine green.

6. The microfluidic device according to claim 1, wherein a color of the particle-shaped component belongs to a black color group or a green color group.

7. The microfluidic device according to claim 1, wherein a content ratio of the particle-shaped component in the wall layer to the other remaining contents of the wall layer is 0.5 mass % (wt %) to 60 wt %.

8. The microfluidic device according to claim 1, wherein the electromagnetic wave has a peak wavelength in a wavelength range of 350 to 700 nm.

9. The microfluidic device according to claim 1, wherein the particle-shaped component is to absorb a fluorescent electromagnetic wave from the base plate.

10. The microfluidic device according to claim 1, wherein the base plate is made of glass.

11. The microfluidic device according to claim 1, wherein the resin forming the wall layer is hydrophobic resin.

12. The sample analysis method according to claim 3, wherein the sample includes a biomolecule, and the wall layer is to absorb an emitted electromagnetic wave emitted from the biomolecule.

\* \* \* \* \*